United States Patent [19]

Metternich

[11] Patent Number: 5,288,707
[45] Date of Patent: Feb. 22, 1994

[54] BOROLYSINE PEPTIDOMIMETICS

[75] Inventor: Rainer Metternich, Inzlingen, Fed. Rep. of Germany

[73] Assignee: Sandoz Ltd., Basle, Switzerland

[21] Appl. No.: 11,443

[22] Filed: Jan. 29, 1993

Related U.S. Application Data

[63] Continuation of Ser. No. 743,847, Aug. 12, 1991, abandoned.

[30] Foreign Application Priority Data

Aug. 13, 1990 [GB] United Kingdom .................. 9017694

[51] Int. Cl.$^5$ .......................... A61K 37/02; C07K 5/10
[52] U.S. Cl. .......................................... 514/19; 514/18; 514/64; 530/330; 530/331; 548/110
[58] Field of Search ............................. 514/18, 19, 64; 530/330, 331; 548/110

[56] References Cited

U.S. PATENT DOCUMENTS 4,963,655 10/1990 Kinder et al. ...................... 530/331

FOREIGN PATENT DOCUMENTS

89/09612 10/1989 PCT Int'l Appl. .
91/16339 10/1991 PCT Int'l Appl. .

*Primary Examiner*—Ronald W. Griffin

[57] ABSTRACT

Borolysine peptidomimetics of formula I

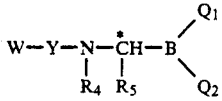

wherein W, Y, $R_4$, $R_5$, $Q_1$ and $Q_2$ are defined in claim 1 are potent thrombin inhibitors.

13 Claims, No Drawings

BOROLYSINE PEPTIDOMIMETICS

This is a continuation of application Ser. No. 07/743,847, filed Aug. 12, 1991, now abandoned.

This invention relates to inhibitors of serine proteases such as thrombin, factor Xa, kallikrein and plasmin as well as other serine proteases like prolyl endopeptidase and Ig AI Protease. Thrombin, the last enzyme in the coagulation system, cleaves soluble fibrinogen to fibrin, which is then crosslinked and forms an insoluble gel forming the matrix for a thrombus. When a vessel is damaged, the above process is necessary to stop bleeding. Under normal circumstances there is no measurable amount of thrombin present in plasma. Increase of the thrombin concentration can result in formation of clots, which can lead to thromboembolic disease, one of the most common serious medical problems of our time.

Thrombin contributes to haemostatic control by means of several biological reactions. In addition to its primary function, the conversion of fibrinogen to fibrin, thrombin activates Factor XIII, which is responsible for the crosslinking of fibrin. Thrombin also acts by means of a positive feed back mechanism involving the activation of Factors V and VIII, which both are necessary for its own formation from prothrombin. Thrombin has another essential role: its binding to platelets initiates platelet release and aggregation which is responsible for primary haemostasis.

The reactions of thrombin are further controlled by natural inhibitors in plasma. The most important of these are antithrombin III and heparin. These two compounds have been isolated and are therapeutically and prophylactically used in conditions where there is an imbalance in the haemostatic mechanism with risk for prothrombin activation.

Synthetic thrombin inhibitors, having oral activity, would be useful as alternatives to the parenteral administration of these natural inhibitors. Much research in this area has resulted in the synthesis of good inhibitors of thrombin in vitro, but as yet there is no really good candidate for oral therapeutic use. By imitating amino acid sequences of fibrinogen, the important natural substrate of thrombin, several good short peptide substrates for thrombin have been produced. These peptide substrates have also been transformed into inhibitors of the enzyme. Thus, the chromogenic substrates D-Phe-Pro-Arg-pNA and D-Phe-Pip-Arg-PNA mimic the sequence preceding the bond split by thrombin. The corresponding reversible and irreversible inhibitors, D-Phe-Pro-Arginal and D-Phe-Pro-Arg-CH$_2$Cl show inhibition in vitro in the $10^{-8}$M range.

Chloromethylketones are generally too nonspecifically reactive to be ideal for therapeutic use, and the peptide aldehyde exemplified above has quite a low LD$_{50}$ value.

Factor Xa is the coagulation enzyme responsible for the generation of thrombin by limited proteolysis of its zymogen, prothrombin. On a weight for weight basis factor Xa is at least 10 times more thrombogenic in vivo than thrombin. This arises from the fact that factor Xa is one step above thrombin in the amplifying cascade system, so that one molecule of factor Xa can generate many molecules of thrombin from its precursor. Its protency may also arise from the rather slow removal of factor Xa by the body. Thrombin, unlike factor Xa, is rapidly cleared from circulating blood onto high affinity sites on the vessel wall. The central position of factor Xa at the junction of the intrinsic and the extrinsic pathways should make it a suitable target for modulating the haemostatic mechanism.

Kallikrein is formed from prekallikrein by the action of factor XII, when located on a negatively charged surface. Kallikrein in turn can cleave factor XII to factor XIIa, thereby forming a reciprocal activation system. Factor XIIa is the first enzyme of the intrinsic part of the coagulation system. The significance of the contact system is probably as a surface mediated defense mechanism, and a large scale activation of the system is normally seen during shock or disseminated intravascular coagulation (DIC). The role of kallikrein at this stage is to cleave high molecular weight kininogen with the release of the vasodilator, bradykinin. Bradykinin also causes increased vascular permeability, pain and migration of the neutrophil leucocytes. Inhibitors of kinin formation have been shown to be beneficial in certain types of inflammation, including arthritis and pancreatitits, and may be useful also in the treatment of asthma. The only substance that has attained clinical significance as a kallikrein inhibitor, is aprotinin (Trasylol). Aprotinin is a polypeptide of molecular weight 6.500, and forms a stable complex with proteases, having a binding constant of $10^{-10}$–$10^{-13}$M.

Fibrinolysis is the process which causes an enzymatic dissolution of fibrinogen and fibrin clots. Plasma contains a protein, plasminogen, which under the influence of various activators is converted to plasmin, a proteolytic enzyme, the activity of which resembles that of trypsin. Plasmin breaks down fibrinogen and fibrin to fibrin/fibrinogen degradation products.

Under normal conditions, the fibrinolysis system is in balance with the coagulation system. Small thrombi formed in the blood stream can be dissolved enzymatically and the circulation through the vessels can be restored by the activation of the fibrinolytic system in the body. If the fibrinolytic activity is too high, it may cause or prolong bleeding. The activity can be inhibited by natural inhibitors in the blood.

Prolyl endopeptides cleaves peptide bonds on the carboxyl side of proline residues within a peptide chain. It is a serine protease which readily degrades a number of neuropeptides including substance P, neurotensin, thyrotropin-releasing hormone and luteinizing hormone-releasing hormone and which has been associated with the ability of cell to produce interleukin 2 (IL-2). The enzyme is inhibited by benzyloxycarbonyl-prolyl-prolinal with a Ki of 14 nM. Despite the fact that almost nothing is known about the physiological role of prolyl endopeptidase, it may play a prominent role in the regulation of the biological activities of various neuropeptides.

The Ig A proteinase-catalyzed cleavage of Ig A, the predominant form of antibody which comprises the first line of defense against infection, separates the Fc from the antigen-binding Fab regions of the molecule. Such cleavage would be expected to impair or abolish its antimicrobial activity. All Ig A proteinases identified thus cleave after a proline residue within the hinge region of human Ig A. Peptide prolyl-boronic acids inhibit Ig A 1 proteinases from Neisseria gonorrhoea and Hemophilus influenzae indicating these enzymes belong to the serine protease family of proteolytic enzymes.

The multiple roles played by thrombin in a variety of physiological processes which have been associated with pathological disorders such as cancer, inflammation and neuronal activity, suggest a potential use of thrombin inhibitors in several indications not strictly related to the cardiovascular system.

Many tumor cells have been shown to elicit procoagulant activity associated with the generation of thrombin. As a consequence, local fibrin deposition and coagulation occur which are thought to be important for the growth of the tumor. Additionally, due to its effects on endothelial cells, thrombin may facilitate the extravasation of tumor cells during metastasis. Hence, thrombin inhibitors may prove beneficial not only in the treatment of certain cancers but also in reducing the hypercoagulability frequently observed in patients during therapy with chemotherapeutic agents.

Thrombin activation of endothelial cells induces a number of pro-inflammatory changes such as synthesis and release of interleukin-1, prostaglandins and platelet-activating factor. Additionally, thrombin induces the exposure of GMP-140 and CD63, two adhesive molecules responsible for the adhesion of leukocytes to the endothelial surface. Thrombin also increases the vascular permeability to proteins, an action which involves neutrophils, and cleaves the interleukin-8-precursor protein, a peptide supposed to be involved in respiratory disorders, rheumatoid arthritis and ulcerative colitis.

Its involvement in all these pro-inflammatory processes makes thrombin to a potential target for the therapeutic treatment with thrombin inhibitors of inflammation-related pathological disorders.

The activity of the protease nexin-1, a modulator of nerve growth and a specific natural thrombin antagonist, is markedly and specifically decreased in patients with Alzheimer's disease. This, together with the observation that thrombin-like activity was increased in the Alzheimer's brains, suggests that thrombin inhibitors may have potential for limiting or reversing neuronal pathological changes associated with thrombin hyperactivity.

Boronic acids have been studied as inhibitors of various serine esterases and proteases. The first boronic acid-containing amino acid analog to be used as a protease inhibitor was the boronic acid analog of N-acetyl L-phenylalanine, which was used as an inhibitor of chymotrypsin and subtilisin. Peptide boronic acids have been used as inhibitors of chymotrypsin, subtilisin, and elastases.

The interaction of boronic acids with proteases in biological systems is known and various simple boronic acids have been shown to be sufficiently nontoxic for use in humans. Peptide boronic acid inhibitors of elastase have recently been used in animal trials in relation to emphysema. Unlike the peptide chloromethylketones, there was no toxicity reported at biologically effective dosage levels.

European Patent Application 293 881 describes the preparation of peptides comprising C-terminal boronic acid derivatives of lysine, ornithine and arginine, and their use as inhibitors of trypsin-like serine proteases. The other amino acids in the peptides are all either the D- or the L-forms of the 20 naturally-occurring amino acids.

It has now been found that compounds, having superior properties as inhibitors of trypsin-like serine proteases, are obtained when the peptide contains at least one unnatural α-amino acid having a hydrophobic side chain.

Accordingly, the present invention provides compounds of formula I

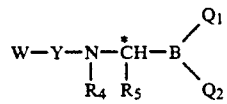

wherein
W = H or an N-protecting group;
Y is a sequence of n amino acids selected such that the n+1 amino acid peptide Y-Lys or Y-Arg has an affinity for the active site of a trypsin-like protease, where n is an integer from 1 to 10 preferably 1 to 4, and in which at least one amino acid is an unnatural amino acid having a hydrophobic side chain;
$Q_1$ and $Q_2$, which may be the same or different, are selected from —OH, —$COR_1$, —$CONR_1R_2$, —$NR_1R_2$, and —$OR_3$, or $Q_1$ and $Q_2$ taken together form a diol residue; $R_1$, $R_2$ and $R_3$, which may be the same or different, are $C_{1-10}$ alkyl, $C_{6-10}$ aryl, $C_{6-10}$ aralkyl, or phenyl substituted by up to three groups selected from $C_{1-4}$ alkyl, halogen and $C_{1-4}$ alkoxy;
$R_4$ is hydrogen or $C_{1-10}$alkyl $R_5$ is a group —A—X wherein A is —$(CH_2)_z$—in which z is 2, 3, 4 or 5; —$CH(CH_3)$—$(CH_2)_2$—; —$CH_2$—$CH(CH_3)$—$CH_2$—; —$(CH_2)_2$—$CH(CH_3)$—$(CH_2)_3$—; —$CH_2$—$CH(CH_3)$—$(CH_2)_2$—; —$CH_2$—$CH_2$—$CH(CH_3)$—$CH_2$; $(CH_2)_3$—$CH(CH_3)$—; —$(CH_2)_3$—$C(CH_3)_2$: $C_{6-10}$aryl, $C_{6-10}$aralkyl and X is —$NH_2$, —$NH$—$C(NH)$—$NH_2$, —$S$—$C(NH)$—$NH_2$, —$N_3$, $C_{1-4}$ alkoxy, $C_{1-4}$ alkylthio, or —$Si(CH_3)_3$ or $R_4$ and $R_5$ together form a trimethylene group and the asymmetric carbon atom marked * may have the D- or L-configuration, or represent any mixture of these.

By an unnatural amino acid is meant any amino acid other than D- or L- Ala, Arg, Asp, Cys, Gln, Glu, Gly, His, Ile, Leu, Lys, Met, Phe, Pro, Ser, Thr, Trp, Tyr, or Val.

Preferably the N-protecting group W is of formula $H(CH_2CH_2O)_p$— where p=3–30; $R_6CO$—; $R_7OCO$— or $R_8SO_2$— in which $R_6$ is $C_{1-6}$ alkyl; $R_7$ is $C_{1-6}$ alkyl, phenyl, benzyl or naphthyl; and $R_8$ is phenyl, naphthyl or $C_{1-4}$ alkylphenyl; of which $R_7OCO$— is preferred. The most preferred protecting groups are those of formula $R_7'OCO$— in which $R_7'$ is tert-butyl (designated Boc), and in which $R_7'$ is benzyl (designated Z).

Preferably $R_5$ is $R_5'$ where $R_5'$ is —$(CH_2)_{z'}$—X', in which X' is —$NH_2$, —$NH$—$C(NH)$—$NH_2$, —$N_3$ or —$Si(CH_3)_3$, and z' is 2, 3 or 4.

Preferred compounds are those of formula Ia

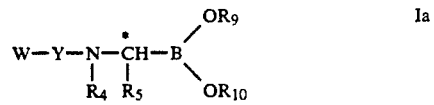

wherein: W, Y, $R_4$ and $R_5$ are as defined above and $R_9$ and $R_{10}$ represent the residue of a dihydroxy compound.

Useful examples are, 2,3-butanediol; catechol; 2,3-dimethylbutandiol-2,3; cyclohexanediol; ethylene glycol; 1,2-hexanediol; 2,3-hexanediol; diethanolamine or aliphatic or aromatic compounds having hydroxy groups that are substituted on adjacent carbon atoms or on carbon atoms substituted by another carbon atoms.

Particularly preferred are those compounds in which $Q_1$ and $Q_2$ taken together represent the group OPin of formula a) or the group of formula b)

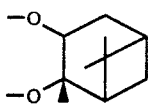  a)

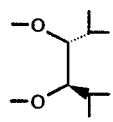  b)

The amino acids constituting Y are α-amino acids which may be selected from the L-amino acids naturally occurring in proteins, their corresponding enantiomeric D-amino acids or chemically modified alpha-amino acids such as glutamic acid gamma-piperidide

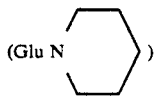

or pipecolic acid (Pip), provided that at least one amino acid is an unnatural amino acid having a hydrophobic side chain.

Preferred unnatural amino acids are of formula II

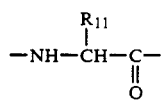  II in which $R_{11}$ is a hydrophobic group. Preferred hydrophobic groups consist of a methylene group linked to an optionally by a polar group substituted aromatic group or an alicyclic group having at least two rings and no polar substituents, or to a tert. butyl or trimethylsilyl group. Preferably $R_{11}$ is $R_{11}'$ where $R_{11}'$ is a group of formulae c), d), e), f), g), h) or i)

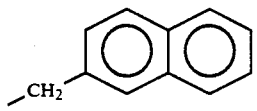  c)

—CH$_2$—Si(CH$_3$)$_3$  d)

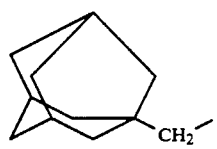  e)

—CH$_2$—C(CH$_3$)$_3$  f)

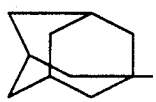  g)

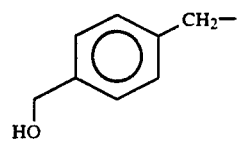  h)

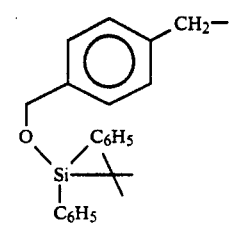  i)

The unnatural amino acids of formula II may be in D- or L-form or any mixture of these, but are preferably in D-form.

More preferred compounds are thrombin inhibitors of formula I in which Y is a sequence of two amino acids, of which the N-terminal amino acid is the unnatural amino acid and the other amino acid is L-proline (Pro), of formula

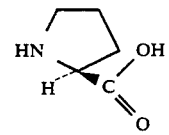

These more preferred compounds have the formula I'

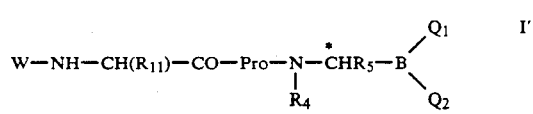  I' in which W, $R_4$, $R_5$, $R_{11}$, $Q_1$ and $Q_2$ are as defined above.

Particularly preferred compounds are those of formula I''

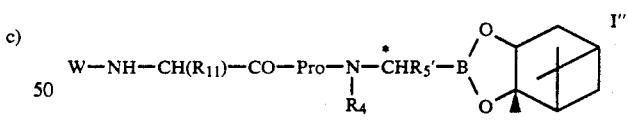  I'' in which W, $R_4$, $R_5'$ and $R_{11}$ are as defined above.

The most preferred compounds are the compound of formula III

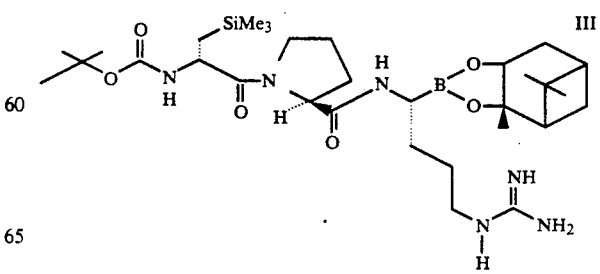  III the compound of formula IV

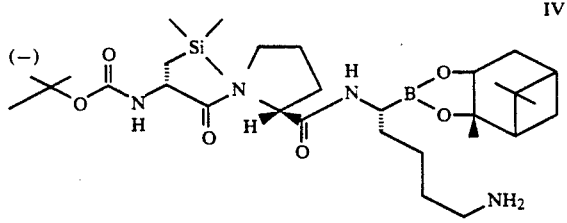

and the compound of formula V

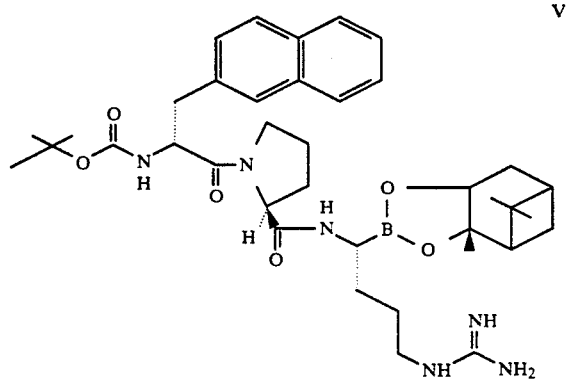

A peptide is considered to have an affinity for the active site of trypsin-like proteases if the particular peptide has a value of $10^{-3}$M or lower for the dissociation constant.

The compounds of formula I in which X is —NH—C(NH)—NH$_2$ may be prepared by reacting a compound of formula I in which X is —NH$_2$ with cyanamide in an organic solvent under strong acid conditions. The compounds in which X is —NH$_2$ may in turn be produced by hydrogenation of a compound of formula I in which X is —N$_3$. Hydrogenation may be carried out under standard conditions using for example a Pd/C catalyst.

The compounds of formula I in which X is —N$_3$ may be produced by reaction of a compound of formula VI

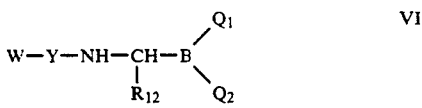

in which W, Y, Q$_1$ and Q$_2$ are defined above and R$_{12}$ is —A—Br wherein A is definded above with sodium azide in a polar aprotic solvent such as dimethyl sulphoxide. Compounds of formula I in which X is an alkylthio group may be produced by the reaction of a compound of formula VI with a thiol in the presence of an organic base such as guanidine.

The intermediates of formula VI, as well as compounds of formula I in which X is —Si(CH$_3$)$_3$ or an alkoxy group may be obtained by the reaction of a compound of formula VII

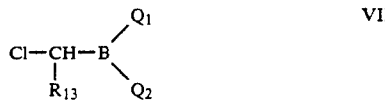

in which Q$_1$ and Q$_2$ are defined above and R$_{13}$ is —A—Br, A—Oalkyl or —A—Si(CH$_3$)$_3$ wherein A is defined above with LiN[Si(CH$_3$)$_3$]$_2$, followed by hydrolysis with 3 mole equivalents of acid and coupling with a protected peptide of formula VIII

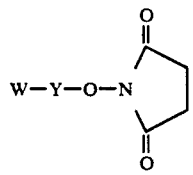

wherein W and Y are defined above

The reaction is preferably carried out in a dry aprotic polar solvent, for example tetrahydrofurane, at a temperature between −78° C. and room temperature.

The intermediates of formula VII may be obtained by the method of Matteson et al, Organometallics 3 1284–8 (1984).

The protected peptide of formula VIII may be prepared by methods which are conventional in peptide chemistry, starting from the desired unnatural amino acid. Such amino acids either are commercially available (for example the amino acid in which R$_{11}$ is the group c) or may be prepared by methods analogous to those described in the literature, e.g. Angew. Chem. 93, 793 (1981) and J. Am. Chem. Soc. 109, 6881 (1987).

The compounds of formula I are useful as inhibitors of trypsin-like proteases and may be used in vitro for diagnostic and mechanistic studies of these enzymes. Furthermore, because of their inhibitory action they are indicated for use in the prevention or treatment of diseases caused by an excess of an enzyme in a regulatory system, for example control of the coagulation of fibrinolysis system.

Those compounds of the invention which are thrombin or factor Xa inhibitors have anti-thrombogenic properties and may be employed when an anti-thrombogenic agent is needed. Generally, these compounds may be administered orally or parenterally to a host to obtain an anti-thrombogenic effect. In the case of larger mammals such as humans, the compounds may be administered alone or in combination with pharmaceutical carriers or diluents at a dose of from 0.02 to 15 mg/Kg of body weight and preferably 1–10 mg/Kg to obtain the anti-thrombogenic effect, and may be given as single dose or in divided doses or as a sustained release formulation. When an extracorporeal blood loop is to be established for a patient, 0.1–1 mg/Kg may be administered intravenously. For use with whole blood from 1–10 mg per liter may be provided to prevent coagulation. Pharmaceutical diluents are well known and include sugars, starches and water which may be used to make tablets, capsules, injectable solutions and the like. The compounds of the invention may be added to blood for the purpose of preventing coagulation of the blood in blood collecting or distribution containers, tubing or implantable apparatus which comes in contact with blood.

The advantages of the compounds of the invention include oral activity, rapid onset of activity and low toxicity. In addition, these compounds may have special utility in the treatment of individuals who are hypersensitive to compounds such as heparin.

In the following examples, the symbols have the following meanings:

Z = benzyloxycarbonyl
Boc = t-butyloxycarbonyl
Ac = acetyl
MeOH = methyl alcohol
EtOAc = ethyl acetate
DCC = dicyclohexylcarbodiimide
HONSu = N-hydroxy-succinimide
OPin = pinanediol
THF = tetrahydrofuran
n-Bu = n-butyl
Np = p-nitrophenyl
TLC = thin layer chromatography
Bzl = benzyl
Baa = —NH—CH—(CH$_2$CH$_2$CH$_2$Br)B—
TMSal = trimethylsilylalanine
Adal = adamantylalanine
Naphal = 2-naphthylalanine
BoroOrn = —NH—CH—(CH$_2$CH$_2$CH$_2$NH$_2$)B—
BoroArg = —NH—CH—[CH$_2$CH$_2$CH$_2$NHC(NH)NH$_2$]B—
Adgly = 1-adamantylglycine
BoroPro- = analog of proline in which the —COOH OPin group is replaced by B-OPin
BoroLys = —NH—CH—(CH$_2$—CH$_2$—CH$_2$—CH$_2$—NH$_2$)B—
BoroHArg = —NH—CH—(CH$_2$CH$_2$CH$_2$CH$_2$NHC(NH)NH$_2$)B—
BoroMpg = —NH—CH—(CH$_2$CH$_2$CH$_2$—OCH$_3$)B—
p-OH-Me-Phal = p-hydroxymethyl-phenylalanine
p-TBDPS-O-Me-Phal = p-tert.butyl-diphenyl-silyl-oxy-methyl-phenylalanine The kinetic parameters $K_i$, $k_{on}$ and $k_{off}$ are determined by the inhibition of the enzyme catalysed hydrolysis of a peptide-arg-pNA. This hydrolysis yelds p-nitroaniline, and its time-dependent release, quantified by the optical density measured at 405 nm, determines the rates of the inhibited and uninhibited reactions.

Kinetic measurements are performed on a 96-microwell plate in combination with a single-cell kinetic reader. Active-site titrated human thrombin is dissolved in 0.1M phosphate buffer, pH 7.4, containing 0.1M NaCl and 0.1% bovine serum albumin to a stock solution containing 400 nM active enzyme. For the chromogenic assay this solution is dissolved in the same buffer to 0.4 nM. The substrate, 2AcOH—H-D-cyclohexyl-ala-arg-pNA is dissolved in the same buffer to 0.5 mM concentration. Inhibitors are first dissolved in cremophor/ethanol 1:1 and then diluted with dist. water to 1 mM stock solution. Further dilutions are performed with the phosphate buffer described above.

Assays are initiated by adding 100 μl enzyme solution to a mixture containing 100 μl inhibior and 50 μl substrate solution. The release of p-nitroaniline from the hydrolysis of the peptidyl p-nitroanilide substrates is followed for 30 min to 1 h by measuring the increase in optical density at 405 nm. The collected data are used to calculate the kinetic parameters in the presence and in the absence of the inhibitor. Although other mechanisms of action are not excluded, the characterization of this class of thrombin inhibitors is restricted to the two major mechanisms observed, namely to fast, reversible and slow-, tight-binding competitive inhibition. Kinetic constants of those inhibitors displaying fast, reversible binding mechanism, namely fast binding (initial rate $v_0$ of control > $v_0$ with inhibitor) at $I_t >> E_t$ (total inhibitor concentration/total enzyme concentration) are calculated by linear regression fitting from a 1/v vs. inhibitor concentration [I] plots. The $K_i$ value is calculated from the horizontal intercept $K_{i,app}$ by equation (1)

$$K_{i,app} = K_i (1 + S/K_m) \quad (1)$$

If the rate of interaction with the enzyme is slow ($v_0$ not affected by the inhibitor) and tight ($K_i$ close to or lower than $E_t$) so that the inhibited steady-state velocity is only slowly achieved, the progress curce of pNA formation is described by $$P = V_s t + \frac{(V_0 - V_s)}{k_{obs}} [1 - \exp(-k_{obs} t)] \quad (2)$$

where P is the amount of pNA formed at time 't', $V_0$ the initial rate, $V_s$ the rate at steade-state, and $k_{obs}$ an apparent global reaction rate as a function of $E_t$, $I_t$, $K_{i,app}$, and the observed second-order rate constant ($k'_{on}$) for the interaction between inhibitor and enzyme. Data from slow, tight-binding inhibition measurements are fitted to equation (2) by a nonlinear regression analysis which yields estimates of $k_{obs}$. Values for $k'_{on}$, $k_{off}$ and $K_{i,app}$ are then obtained from a plot $k_{obs}$ vs [I]. The value for $k_{off}$ is given by the vertical intercept, while the values of $k'_{on}$ and $K_i$ are calculated from the slope and horizontal intercepts, respectively, using equation (1).

EXAMPLE 1

Boc-TMSal-Pro-NH—CH[(CH$_2$)$_3$N$_3$]BOPin

A. Boc-D-TMSal-OH

D-TMSal ethyl ester (21.5 g, 113.7 mMol), prepared according to the procedure given in Angew. Chem. 93, 793 (1981), is dissolved in CH$_2$Cl$_2$ and a solution of an excess of Boc$_2$O in CH$_2$Cl$_2$ is added. After 15 hr at room temperature, 500 ml of ice-cold 0.25N hydrochloric acid is added. The organic layer is washed with 5% NaHCO$_3$ and brine, then is dried over Na$_2$SO$_4$ and concentrated in vacuo.

The crude material (colourless oil) is used directly in the saponification step. It is dissolved in methanol, cooled to 0°, mixed with 510 ml of 1N NaOH and stirred at 0° for 3 hr. After acidification to pH1 with 1N HCl, the mixture is extracted several times with ether. The organic layers are combined, washed with brine, dried over Na$_2$SO$_4$ and concentrated in vacuo. The product (29.7 g oil) is used in the next step without further purification.

B. Boc-D-TMSal-Pro-ONSu

Boc-D-TMSal-OH (29.7 g, 113.7 mMol) and p-nitrophenol (19.0 g, 136.3 mMol) are dissolved in EtOAc. After cooling to 0°, DCC (23.4 g, 113.6 mMol) is added and the mixture is stirred for 1 hr at 0° and then for 15 hr at room temperature. The precipitate is filtered off and washed with EtOAc and the filtrate is concentrated in vacuo. The resulting oil is purified by flash chromatography (9:1 hexane/EtOAc) to give the desired Boc-D-TMSal-ONp as white crystals.

Boc-D-TMSal-ONp (51.6 g, 113.7 mMol) is dissolved in THF and an aqueous solution of equimolar amounts of proline and Et$_3$N is added. After 20 hr at room temperature, the THF is removed in vacuo and the aqueous residue is diluted with water and then extracted several times with EtOAc. The pH of the aqueous layer is adjusted to 3 by adding 10% citric acid. The resulting oily product is extracted several times with EtOAc.

The combined organic layers are washed with brine, dried over $Na_2SO_4$ and concentrated in vacuo. The colourless oil is recrystallized from ether/hexane to give the dipeptide Boc-D-TMSal-Pro-OH as a white crystalline compound mp: 176° C.

The resulting dipeptide (26.0 g, 72.5 mMol( is dissolved in EtOAc. After cooling to 0°, HONSu (9.8 g, 85.5 mMol) and DCC (14.9 g, 72.3 mMol) are added. The mixture is stirred for 3 hr at 0° and then for an additional 15 hour at room temperature. The mixture is recooled to 0°, the dicyclohexylurea is filtered off and washed several times with EtOAc. The filtrate is washed with aqueous 0.1M $Na_2CO_3$ and then with aqueous 2% $KHSO_4$.

After drying over $Na_2SO_4$ and concentration in vacuo, Boc-D-TMSal-Pro-ONSu is obtained as a white foam.

C) Boc-D-TMSal-Pro-Baa-OPin

This procedure is a one-pot 3-step procedure which comprises the in situ formation of a chiral α-(bistrimethylsilyl)amido boronate, the hydrolysis of the two trimethylsilyl groups and the coupling of the so formed α-amino boronate with the active ester (Boc-D-TMSal-Pro-ONSu) prepared in step B. The entire sequence of reactions is carried out under an argon atmosphere. The chiral α-chloro boronate ((+)-Pinanediol-(S)-1-chloro-4-bromo-butane-1-boronate) (1.75 g, 5.0 mMol) is dissolved in 2.5 ml THF and is added to a precooled (−78°) solution of lithium hexamethyldisilazane (5 ml of a 1.0M solution in hexane, 5.0 mMol). After stirring for 30 minutes at −78°, the solution is warmed up overnight to room temperature. After recooling to −78°, 3 mol equivalents of HCl in dioxane are added. The mixture is warmed up to room temperature and is stirred for 2 hr at this temperature. After recooling to −20°, a solution of the active ester of step B (2.28 g, 5.0 mMol) in 6 ml $CH_2Cl_2$ is added, followed by the addition of 1.39 ml (10.0 mMol) of triethylamine.

The mixture is stirred for 1 hr at −13°, warmed up to room temperature and stirred for 2 hr at this temperature. The mixture is filtered, the filtrate is concentrated in vacuo, the residue is diluted with ether and washed with 2N HCl, 5% $NaHCO_3$ and brine. The organic layer is dried over $Na_2SO_4$ and concentrated in vacuo. The residue crystallized on standing to give the desired chiral peptide boronate as a white crystalline compound.

D) Boc-D-TMSal-Pro-NH—CH[$(CH_2)_3N_3$]BOPin

Boc-D-TMSal-Pro-Baa-OPin, the product of step C (804 mg, 1.2 mMol) is dissolved in 13 ml of DMSO and sodium azide (156 mg, 2.4 mMol) is added. The mixture is stirred for 3 hours at room temperature. Ether/ice water is added, and immediately white crystals are precipitated out of the mixture. The white precipitate is filtered off and washed with ether to give 0.6 g of the azide as a white crystalline compound.

EXAMPLE 2

Boc-D-TMSal-Pro-BoroOrn-OPin

The azide of Example 1 (569 mg, 0.9 mMol) is dissolved in 25 ml EtOAc and is hydrogenated in the presence of 0.5 g of 10% Pd/C. After 2.5 hr, catalyst is removed and the solution is concentrated in vacuo to yield a white foam, which is recrystallized from EtOAc/ether to give the desired product as a white crystalline compound, m.p.: 200°-202°, $[\alpha]_D^{20} = -11.6°$ (c=0.5 in MeOH).

EXAMPLE 3

Boc-D-TMSal-Pro-boroArg-OPin (benzene sulfonate)

Boc-D-TMSal-Pro-boroOrn-OPin of Example 2 (250 mg, 0.412 mMol) is dissolved in 2 ml ethanol. Benzene sulphonic acid (65.2 mg, 0.412 mMol) is added. After stirring for 15 minutes at room temperature, cyanamide (86.6 mg, 2.06 mMol) is added and the mixture is heated under reflux. The progress of the reaction is monitored by RP-TLC in which the disappearance of the ninhydrin spot for the amine starting material and the appearance of the Sakaguchi streak of the product is observed. After 7 days, amine can no longer be detected and the solution is concentrated in vacuo. The residue is dissolved in MeOH and is chromatographed on a 5×55 cm column of Sephadex LH-20 with MeOH.

The desired product is obtained as a white foam, $[\alpha]_D^{20} = -45.3°$ (c=1 in $CH_2Cl_2$).

EXAMPLE 4

Boc-D-TMSal-Pro-NH—CH(($CH_2$)$_3$$N_3$)B-OPin

A) (+)-pinanediol-(S)-1-chloro-5-bromo-pentane-1-boronate

4-Bromo-1-butene (20.8 ml, 203.3 mMol) is reacted with catecholborane (24,4 g, 203,3 mMol) at 100° C. over 16 hr. The crude product is distilled in vacuo to give 4-bromo-butane-1-boronate as a white crystalline compound. (+)-Pinanediol (27.7 g, 163 mMol) is dissolved in THF and the above synthesized 4-bromo-butane-1-boronate (41.6 g, 163 mMol) is added. After 1 hr at room temperature, the THF is removed in vacuo and the residue is purified by flash chromatrography (90:10 hexane/EtOAc) to give (+)-pinanediol-4-bromo-butane-1-boronate as a colourless oil.

The desired (+)-pinanediol-(S)-1-chloro-5-bromo-pentane-1-boronate is prepared according to the procedure given in Organometallics 3, 1284 (1984). Therefore methylenechloride (9.8 ml) in THF is cooled to −100° C. and n-butyllithium (71.6 ml 1.6M solution, 114.5 mMol) is added over 20 min. After 15 min at −100° C., a cold (−78° C.) solution of (+)-pinanediol-5-bromo-pentane-1-boronate (32,8 g, 104.1 mMol) in THF is added. After additional 1 hr at −100° C. anhydrous $ZnCl_2$ (7.1 g, 52,0 mMol) in THF is added. After additional 15 min at −100° C. the reaction mixture is warmed to room temperature and stirred for 2 hr at this temperature. The solvent is removed in vacuo, the residue is diluted with hexane/water and is extracted several times with hexane. After drying over $Na_2SO_4$ and removal of the solvent in vacuo, (+)-pinanediol-(S)-1-chloro-5-bromo-pentane-1-boronate is obtained as a yellow oil which is used directly in the next step without further purification.

B) Boc-D-TMSal-Pro-NH—CH(($CH_2$)$_4$Br)B-OPin

A solution of LiN(SiMe$_3$)$_2$ (65.2 ml 1.0M solution, 65.2 mMol) in THF is cooled to −78° C. The α-chloroboronate of step A) (23.7 g, 65.2 mMol) in THF is added. After stirring for 1 hr at −78° C., the mixture is stirred for 15 hr at room temperature. After this periode, the reaction mixture is recooled to −78° C., HCl (29.8 ml 6.56N solution, 196 mMol) in dioxan is added, the solution is stirred for 45 min at −78° C. and then for 2 hr at room temperature. The mixture is cooled to −15° C., Boc-TMSal-Pro-ONSu (29.7 g, 65.2 mMol) of Example 1 in CH₂Cl₂ is added before triethylamine (18.1 ml, 130.4 mMol) is added to start the coupling reaction. After stirring at −15° C. for 1 hr, the mixture is stirred for 2 hr at room temperature. The mixture is filtered over Hyflo and is concentrated in vacuo. The residue is diluted with ether/water and is extracted several times with ether. After drying over Na₂SO₄ and concentration in vacuo the desired Boc-D-TMSal-Pro-NH—CH((CH₂)₄Br)B-OPin is obtained after crystallization from ether/hexane as a white crystalline compound, mp: 74° C.

C) Boc-D-TMSal-Pro-NH—CH((CH₂)₄N₃)B-OPin

The product of step B) (33.3 g, 48.6 mMol) is dissolved in DMSO and sodium azide (6.3 g, 97.2 mMol) is added. The mixture is stirred for 6 hr at room temperature. Ether/ice water is added, and the mixture is extracted several times with ether. After drying over Na₂SO₄ and concentration in vacuo the resulting oil is crystallized to give Boc-D-TMSal-Pro-NH—CH((CH₂)₄N₃)B-Pin as a white crystalline compound, mp: 69°–70° C.; $\alpha_D = -74.4°$ (c=1.0 in MeOH).

EXAMPLE 5

Boc-D-TMSal-Pro-BoroLys-OPin

The azide of Example 4 (22.0 g, 34.0 mMol) is dissolved in EtOAc and is hydrogenated in the presence of 4.0 g of 10% Pd/C. After 9 hr, the catalyst is removed and the solution is concentrated in vacuo. The resulting foam is dissolved in EtOAc and is crystallized to give the desired Boc-D-TMSal-Pro-BoroLys-OPin as white crystals, mp: 128°–129° C.; $\alpha_D = -59.6°$ (c=1.0 in MeOH).

EXAMPLE 6

Boc-D-TMSal-Pro-BoroHArg-OPin (benzene sulfonate)

The benzene sulfonate of Boc-D-TMSal-Pro-Boro-Lys-OPin of Example 5 (800 mg, 1.03 mMol) is dissolved in ethanol. Cynamide (210 mg, 5.0 mMol) is added and the mixture is heated under reflux. The progress of the reaction is monitored by RP-TLC in which the disappearance of the ninhydrin spot for the amine starting material and the appearance of the Sakaguchi streak of the product is observed. After 7 days, amine can no longer be detected and the solution is concentrated in vacuo. The residue is dissolved in MeOH and is chromatographed on a 5×55 cm column Sephadex LH-20 with MeOH.

The desired product is obtained as a white foam, $\alpha_D = -40.8°$ (c=0.5 in CH₂Cl₂).

EXAMPLES 7–29

By methods analogous to those in Examples 1–6, the compounds of formula

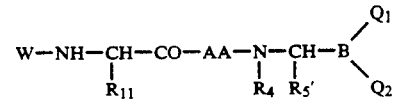

in which $R_4$, $R_5'$, $R_{11}$, $Q_1+Q_2$ and AA have the significances shown in the following table I can be obtained

TABLE I

| Ex | W | $R_{11}$ | $R_4$ | $R_5'$ | $Q_1+Q_2$ | AA | $[\alpha]_D^{20}$ | C | solvent |
|----|---|---|---|---|---|---|---|---|---|
| 7  | Boc | c) | H | —(CH₂)₃—NH₂ | a) | Pro | −27,8° | 0,5 | EtOH |
| 8  | Boc | c) | H | —(CH₂)₃NHC(NH)NH₂ | a) | Pro | −75,0° | 1,0 | CH₂Cl₂ |
| 9  | Boc | e) | H | —(CH₂)₄N₃ | a) | Pro | −64,7° | 0,51 | CH₂Cl₂ |
| 10 | Boc | e) | H | —(CH₂)₂SiMe₃ | a) | Pro | −57,0° | 0,5 | CH₂Cl₂ |
| 11 | Boc | d) | H | —(CH₂)₂SiMe₃ | a) | Pro | −59,3° | 1,0 | CH₂Cl₂ |
| 12 | Ac  | c) | H | —(CH₂)₃NHC(NH)NH₂ | a) | Pro | −80,2° | 0,5 | CH₂Cl₂ |
| 13 | Boc | e) | H | —(CH₂)₃NHC(NH)NH₂ | a) | Pro | −42,3° | 0,5 | CH₂Cl₂ |
| 14 | Boc | c) | H | —(CH₂)₄NHC(NH)NH₂ | a) | Pro | −18,8° | 0,5 | EtOH |
| 15 | Boc | e) | H | —(CH₂)₄NHC(NH)NH₂ | a) | Pro | −61,7° | 0,41 | CH₂Cl₂ |
| 16 | Boc | e) | H | —(CH₂)₄NH₂ | a) | Pro | −52,4° | 0,54 | CH₂Cl₂ |
| 17 | Boc | d) | H | —(CH₂)₃NHC(NH)NH₂ | b) | Pro | −35,8° | 1,0 | EtOAc |
| 18 | Boc | e) | H | —(CH₂)₃—NH₂ | a) | Pro | −10,6° | 0,5 | CH₂Cl₂ |
| 19 | Boc | d) | H | —(CH₂)₃NHC(NH)NH₂ | b) | Gly | +8,8° | 0,5 | EtOAc |
| 20 | Ac  | c) | H | —(CH₂)₃—NH₂ | a) | Pro | −78,6° | 0,75 | CH₂Cl₂ |
| 21 | Boc | e) | H | —(CH₂)₃—NH₂ | b) | Gly | −4,4° | 0,5 | CH₂Cl₂ |
| 22 | Boc | f) | H | —(CH₂)₃—N₃ | a) | Pro | −76,0° | 0,5 | CH₂Cl₂ |
| 23 | Boc | f) | H | —(CH₂)₃—NH₂ | a) | Pro | −25,4° | 0,5 | CH₂Cl₂ |
| 24 | Boc | f) | H | —(CH₂)₃NHC(NH)NH₂ | a) | Pro | −34,8° | 0,5 | CH₂Cl₂ |
| 25 | Boc | d) | H | —(CH₂)₄NHC(NH)NH₂ | a) | Gly | −14,7° | 1,0 | MeOH |
| 26 | Boc | d) | H | —(CH₂)₄NH₂ | a) | Gly | −30,6 | 0,5 | EtOH |
| 27 | Boc | d) | H | —(CH₂)₄NH₂ | a) | Asp | −18,4° | 0,5 | MeOH |
| 28 | H   | d) | H | —(CH₂)₃NH₂ | a) | Pro | −53,6 | 0,32 | MeOH |
| 29 | Boc | d) | H | —(CH₂)₄OC₂H₅ | a) | Pro | −54,2 | 0,5 | MeOH |

EXAMPLE 30

Boc-D-TMSal-Pro-BoroMpg-OPin

A)

(+)-Pinanediol-(S)-1-chloro-4-methoxy-butane-1-boronate

3-Methoxy-1-propene (6.0 g, 83.3 mMol) is reacted with catecholborane (10.0 g, 83.3 mMol) at 100° C. over 24 hr. The crude product is distilled in vacuo to give 3-methoxy-propane-1-boronate as a colourless oil. (+)-Pinanediol (10.6 g, 62.5 g mMol) is dissolved in THF and the above synthesized 3-methoxy-propane-1-boronate (12.0 g, 62.5 mMol) is added. After 1 hr at room temperature, the THF is removed in vacuo and the residue is purified by flash chromatography (80:20 hexane/EtOAc) to give (+)-pinanediol-3-methoxy-propane-1-boronate as a colourless oil.

The desired (+)-pinanediol-(S)-1-chloro-4-methoxy-butane-1-boronate is prepared according to the procedure given in Organometallics 3, 1284 (1984). Therefore methylenechloride (2.2 ml) in THF is cooled to −100° C. and n-butyllithium (13.8 ml 1.6M solution, 22.0 mMol) is added over 20 min. After 15 min at −100° C., a solution of (+)-pinanediol-3-methoxy-propane-1-boronate (5.04 g, 20 mMol) in THF is added followed by anhydrous ZnCl$_2$ (1.42 g, 10.0 mMol). After additional 15 min at −100° C. the reaction mixture is warmed to room temperature and stirred for 2 hr at this temperature. The solvent is removed in vacuo, the residue is diluted with ether and washed with water. The organic layer is dried over Na$_2$SO$_4$ and is concentrated to give an oil which is purified by flash chromatography (9:1 hexane/EtOAc) to give the desired (+)-pinanediol-(S)-1-chloro-4-methoxy-butane-1-boronate as a colourless oil.

B) Boc-D-TMSal-Pro-BoroMpg-OPin

A solution of LiN(SiMe$_3$)$_2$ (5 ml 1.0M solution, 5.0 mMol) in THF is cooled to −78° C. The α-chloroboronate of step A) (1.53 g, 5.0 mMol) in THF is added. After stirring for 1 hr at −78° C., the mixture is stirred for 15 hr at room temperature. After this periode, the reaction mixture is recooled to −78° C., HCl (2.7 ml 5.65N solution, 15.0 mMol) in dioxan is added, the solution is stirred for 30 min at −78° C. and then for 2 hr at room temperature. The mixture is cooled to −15° C., Boc-TMSal-Pro-ONSu (2.28 g 5.0 mMol) of Example 1 in CH$_2$Cl$_2$ is added before triethylamine (1.39 ml, 10.0 mMol) is added to start the coupling reaction. After stirring at −15° C. for 1 hr, the mixture is stirred for 2 hr at room temperature. The mixture is filtered over Hyflo and is concentrated in vacuo. The residue is diluted with EtOAc and is washed with 0.2N HCl, 5% NaHCO$_3$ and finally with brine. After removal of the solvent, an oil is obtained which is purified by flash chromatography (EtOAc) to give Boc-D-TMSal-Pro-BoroMpg-OPin as a white foam, $\alpha_D = -48.8°$ (c=0.25 in CH$_2$Cl$_2$).

EXAMPLE 31

Boc-D-(p-(TBDPS-O)methyl)Phal-Pro-BoroOrn-OPin

A)
Boc-D-(p-((1,1-dimethylethyl)diphenyl-silyl)oxy)methylphenylalanine

In order to selectively reduce the azido group in the substrate, thiophenol (7.27 g, 66.0 mMol) is added to a suspension of SnCl$_2$ (3.12 g, 16.5 mMol) in CH$_2$Cl$_2$. Triethylamine (6.8 ml, 49.5 mMol) is added and a yellow solution is obtained. Boc-anhydride (4.8 g, 22.0 mMol) is added before (3 (2S), 4S-3-(2-azido-3-(p-((1,1-dimethyl)diphenyl-silyl)oxy-methyl)phenyl-1-oxo-propyl)-4-(phenylmethyl)-2-oxazolidinone (%de>95; 6.8 g, 11.0 mMol), prepared according to the procedure given in J. Am. Chem. Soc. 109 6881 (1987), is added as a solution in CH$_2$Cl$_2$. After stirring for 2.5 hr at room temperature, the mixture is diluted with EtOAc/2N NaOH and filtered over Hyflo. The organic layer is washed with 2% aqueous NaHSO$_4$, 5% aqueous NaHCO$_3$ and finally with brine. After drying over Na$_2$SO$_4$ and concentration in vacuo the obtained yellow oil is purified by flash chromatography to give (3(2S),4S)-3-(2-(((tert.-butyloxy)carbonyl)amino)-3-(p-(((1,1-dimethylethyl)diphenyl-silyl)oxy)-methyl)-phenyl-1-oxo-propyl)-4-(phenylmethyl)-2-oxazolidinone as a white foam. This compound (2.0 g, 2.88 mMol) is dissolved in THF/water an is hydrolyzed with in situ generated LiOOH (5.76 mMol) at 0° C. After 1.75 hr at 0° C., Na$_2$SO$_3$ (1.25 g, 9.9 mMol) in water is added. THF is removed in vacuo, the pH of the residue is adjusted to 1-2 and the mixture is extracted 3 times with EtOAc. The combined organic layers are washed with water, dried over Na$_2$SO$_4$ and are concentrated in vacuo. After crystallization from hexane/ether the oxazolidinone is obtained as white crystals. The filtrate is concentrated in vacuo to give the desired title compound as a white foam.

B)
Boc-D-(p-(((1,1-dimethylethyl)diphenyl-silyl)oxy)-methyl)phenylalanine-Pro-ONSu DCC (0.59 g, 2.88 mMol) is added to a mixture of the title compound of step A) (1.6 g, 2.88 mMol) and p-nitrophenol (0.43 g, 3.12 mMol) in EtOAc at 0° C. The reaction mixture is stirred for 16 hr at room temperature. After cooling to 0° C., the precipitate is filtered off and washed with cold EtOAc. The filtrate is concentrated in vacuo. The resulting oil (Boc-D-(p-TBDPS-O-Me)-Phal-ONp) is used in the next step without further purification. Boc-D-(p-TBDPS-O-Me)-Phal-ONp (2.2 g, 2.88 mMol) is dissolved in THF and an aqueous solution of L-proline (365 mg, 3.17 mMol) and Et$_3$N (0.88 ml, 6.33 mMol) is added. After 15 hr at room temperature the THF is removed in vacuo. The pH is adjusted to 3 by adding 10% citric acid. The resulting oily product is extracted several times with EtOAc. The combined organic layers are washed with brine, dried over Na$_2$SO$_4$ and concentrated in vacuo. The colourless oil is purified by flash chromatography (9:1 CH$_2$Cl$_2$/EtOH to eluate p-nitrophenol, then 80:20 CH$_2$Cl$_2$/EtOH) to give Boc-D-(p-TBDPS-O-Me)-Phal-Pro-OH as a white foam. This dipeptide (1.3 g, 2.06 mMol) is dissolved in EtOAc. After cooling to 0° C., HONSu (220 mg, 2.47 mMol) and DCC (330 mg, 2.06 mMol) are added. The mixture is recooled to 0° C., the dicyclohexylurea is filtered off and washed several times with cold EtOAc. The filtrate is washed with aqueous 0.1M Na$_2$CO$_3$, 8% NaHSO$_4$ and then with brine. After drying over Na$_2$SO$_4$ and concentration in vacuo the title compound Boc-D-(p-TBDPS-O-Me)-Phal-Pro-ONSu is obtained as a white foam.

C) Boc-D-(p-TBDPS-O-Me)-Phal-Pro-Baa-Opin

The title compound is obtained by using the analogous one-pot 3-step procedure described for the synthesis of Boc-D-TMSal-Pro-Baa-OPin in Example 1/C. Therefore the intermediate α-amino-boronate, which results from the reaction of the chiral α-chloro-boronate ((+)-pinanediol-(S)-1-chloro-4-bromo-butane-1-boronate) (659 mg, 2.0 mMol) with LiN(SiMe$_3$)$_2$ (2.0 mMol) and hydrolysis with HCl, is reacted with the active ester of step B) (1.45 g, 2.0 mMol) in the presence of Et$_3$N (4.0 mMol) to give the title compound which is purified by flash chromatography (1:1 hexane/EtOAc).

D) Boc-D-(p-TBDPS-O-Me)-Phal-Pro-BoroOrn-OPin

The product of step C) (680 mg, 0.72 mMol) is dissolved in DMSO and sodium azide (94 mg, 1.44 mMol) is added. The mixture is stirred for 4 hr at room temperature. Ether/ice water is added, and immediately white crystals are precipitated out of the mixture. The white precipitate is filtered off and washed with water to give Boc-D-(p-TBDPS-O-Me)-Phal-Pro-NH-CH((CH$_2$)$_3$N$_3$)B-OPin as a white crystalline compound. This azide (272 mg, 0.3 mMol) is dissolved in EtOAc and is hydrogenated in the presence of Lindlar-Catalyst. After 8 hr, the catalyst is removed and the solution is concentrated in vacuo. The crude product is purified by flash chromatography (EtOAc then EtOH)

to give the desired title compound as a white foam, $\alpha_D = -32.4°$ (c=0.25 in MeOH).

EXAMPLE 32

Boc-D-(p-OH-Me)-Phal-Pro-BoroOrn-OPin

The boro-ornithin of Example 31 (132 mg, 0.15 mMol) is dissolved in THF and is reacted with n-Bu₄NF (0.3 ml 1.1M solution, 0.3 mMol). After 45 min at room temperature ice water is added and the resulting mixture is extracted several times with EtOAc. The combined organic layers are dried over Na₂SO₄ and concentrated in vacuo. The resulting oil is purified by a short chromatography (EtOAc then EtOH) to give the desired title compound as a white foam, $\alpha_D = -34.0°$ C. (c=0.1 in MeOH).

EXAMPLE 33

Boc-D-TMS-al-Adgly-boroPro-OPin

A. L-1-Adamantylglycine (3(2S),4S)-3-(2-Azido-2-adamant-1-yl-1-oxoethyl)-4-(phenylmethyl)-2-oxazolidone (% de>95; 9.86 g, 25.0 mMol), prepared according to the procedure given in J. Am. Chem. Soc. 109, 6881 (1987), is dissolved in 320 ml of a mixture of THF/H₂O (3:1), cooled to 0° C., mixed with 4 equiv. of hydrogen peroxide and 2.0 equiv. of LiOH. The resulting mixture is stirred at 0° C. until the substrate has been consumed (30 min.), and the peroxide (percarboxylate) is quenched at 0° C. with 10% excess of 1.5N aq Na₂SO₃. After buffering with aqueous NaHCO₃ (pH 9–10) the mixture is extracted several times with EtOAc to remove the oxazolidinone chiral auxiliary. The product carboxylic acid is isolated by EtOAc extraction of the acidified (pH 1–2) aqueous phase, drying over Na₂SO₄ and concentration in vacuo. The desired (S)-azido-adamant-1-yl-acetic acid is isolated as white crystals (5.29 g) and is used in the next step without further purification. 2(S)-Azido-adamant-1-ylacetic acid (5.29 g, 22.5 Mmol) is dissolved in 110 ml of EtOH and 11.3 ml of 2N HCl, and is hydrogenated in the presence of 0.7 g of 10% Pd/C. After 2.5 h, catalyst is removed and the solution is concentrated in vacuo to yield the desired aminoacid as the hydrochloride salt. The obtained hydrochloride is suspended in 40 ml of H₂O and is treated with 1.9 g of solid NaHCO₃. The obtained amino acid is filtered off and washed several times with water. After drying in vacuo, L-1-adamantyl-glycine is obtained as a white crystalline compound, $[\alpha]_D^{20} = +3.0$ (c=1.0 in MeOH).

B. Boc-D-TMSal-Adgly-ONSu

Boc-D-TMSal-ONp (7.71 g, 20.2 mMol) of example 1 is dissolved in THF and an aqueous solution of equimolar amounts of 1-adamantylglycine and Et₃N is added. After 20 h at room temperature the THF is removed in vacuo and the aqueous residue is diluted with 150 ml of 0.1N HCl, and then extracted several times with EtOAc. The combined organic layers are washed with brine, dried over Na₂SO₄ and concentrated in vacuo. The oily product is chromatographed on silica gel (CH₂Cl₂) to give the dipeptide Boc-D-TMSal-Adgly-OH as an oil. Boc-D-TMSal-Adgly-OH (6.9 g, 15.2 mMol) is dissolved in 80 ml of EtOAc. After cooling to 0° C., HONSu (2.1 g, 18.0 mMol) and DCC (3.1 g, 15.2 mMol) are added. The mixture is stirred for 3 h at 0° C. and then for an additional 15 h at room temperature. The mixture is recooled to 0° C., the dicyclohexylurea is filtered off and washed with EtOAc. The filtrate is washed with aqueous 0.1M NaHCO₃ and then with aqueous 2% KHSO₄. After drying over Na₂SO₄ and concentration in vacuo, Boc-D-TMSal-Adgly-ONSu (7.2 g) is obtained as a white foam.

C. Boc-D-TMSal-Adgly-boroPro-OPin

The title compound is obtained by using the analogous one-pot 3-step procedure described for the synthesis of Boc-D-TMSal-Pro-Baa-OPin in example 1/C. Due to the low reactivity of the sterically hindered active ester of step B (2.7 g, 5.0 mMol), the intermediate α-amino boronate, which results from the reaction of the chiral α-chloro-boronate ((+)-Pinanediol-(S)-1-chloro-4-bromo-butane-1-boronate) (1.7 g, 5.0 mMol) with lithium hexamethyldisilazane (5.0 mMol) and hydrolysis with HCl, cyclizes to the boroproline derivative, which reacts then with the active ester of step B to give the unexpected Boc-D-TMSal-Adgly-boroPro-OPin as the major product. Flash chromatography (2:1 hexane/EtOAc) of the crude product yields the title compound (0.48 g) as a white foam, which is further purified by recrystallization from ether/hexane to give the desired product Boc-D-TMSal-Adgly-boroPro-OPin as a white crystalline compound.

mp: 187°–188° C., $[\alpha]_D^{20} = +2.8°$ (c=1.0 in CH₂Cl₂).

I claim:

1. A compound of formula I

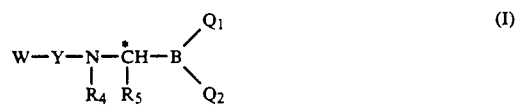

wherein:

W is hydrogen or an N-protecting group

Y is a sequence of n amino acids such that the n+1 amino acid peptide Y-Lys or Y-Arg has an affinity for the active site of a trypsin-like protease; where n is an integer of from 1 to 10 and in which at least one amino acid is an unnatural amino acid having a hydrophobic side chain;

$Q_1$ and $Q_2$ are the same or different and are selected from —OH, —COR₁, —CONR₁R₂, —NR₁R₂ or —OR₃ or —OR₃ or $Q_1$ and $Q_2$ taken together form a diol residue;

R₁, R₂ and R₃ which may be the same or different, are C₁₋₁₀alkyl, C₆₋₁₀aryl, C₆₋₁₀ aralkyl or phenyl substituted by up to three groups selected from C₁₋₄alkyl, halogen and C₁₋₄alkoxy;

R₄ is hydrogen or C₁₋₁₀alkyl

R₅ is a group —A—X; wherein

A is —(CH₂)_z— in which z is 2,3,4 or 5; —CH(CH₃)—(CH₂)₂—; —CH₂—CH(CH₃)—CH₂; —(CH₂)₂—CH(CH₃)—; —(CH₂)₂—C(CH₃)₂—; —CH(CH₃)—(CH₂)₃—; —CH₂—CH(CH₃)—(CH₂)₂—; —CH₂—CH₂—CH(CH₃)—CH₂—; (CH₂)₃—;CH(CH₃)—; —(CH₂)₃—C(CH₃)₂: C₆₋₁₀aryl C₆₋₁₀aralkyl and X is —NH₂, —NH—C(NH)—NH₂, —S—C(NH)—NH₂—, —N₃, C₁₋₄alkoxy, C₁₋₄alkylthio or —Si(CH₃)₃ or R₄ and R₅ together form a trimethylene group and the asymmetric carbon atom marked * may have the D- or L-configuration or represent any mixture of these.

2. A compound according to claim 1 in which W is H(CH$_2$CH$_2$O)$_p$—, R$_6$CO—, R$_7$OCO— or R$_8$SO$_2$—, wherein:

p=3–30
R$_6$=C$_{1-6}$alkyl
R$_7$=C$_{1-6}$alkyl, phenyl, benzyl or naphthyl; and
R$_8$=phenyl, naphthyl or C$_{1-4}$alkylphenyl.

3. A compound according to claim 1 or 2 which is of formula Ia

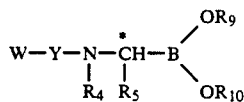

wherein: W, Y, R$_4$ and R$_5$ are as defined in claims 1 or 2 and R$_9$ and R$_{10}$ represent the residue of a dihydroxy compound.

4. A compound according to claim 1 or 2 wherein Q$_1$ and Q$_2$ together represent a group of formula (a) or (b)

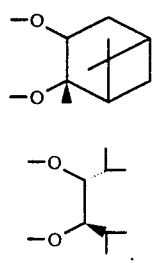

5. A compound according to claims 1 or 2 wherein the unnatural amino acid is of formula II

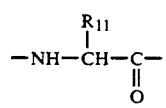

wherein R$_{11}$ is a hydrophobic group.

6. A compound according to claim 5 wherein R$_{11}$ is R$_{11}$' and is a group of formula (c), (d), (e), (f), (g), (h) or (i)

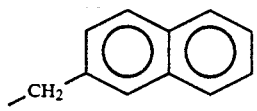

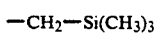

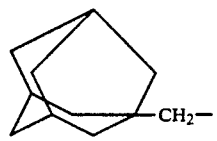

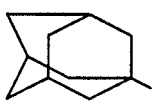

-continued

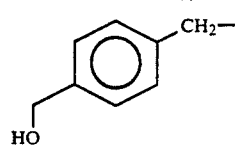

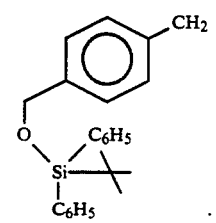

7. A compound according to claim 1 wherein Y is a sequence of two amino acids of which the N-terminal amino acid is the unnatural amino acid and the other amino acid is L-proline.

8. A compound according to claim 1 which is of formula III

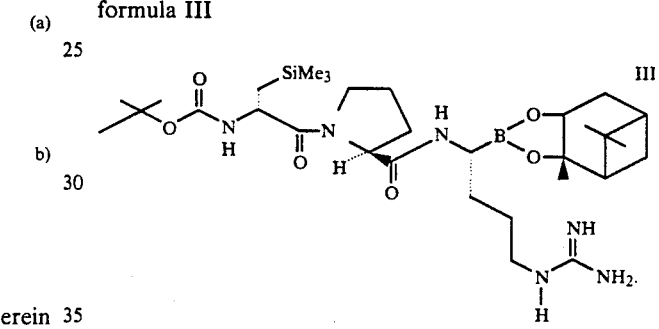

9. A compound according to claim 1 which is of formula IV

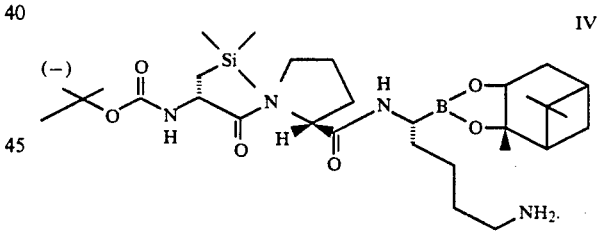

10. A compound according to claim 1 which is of formula V

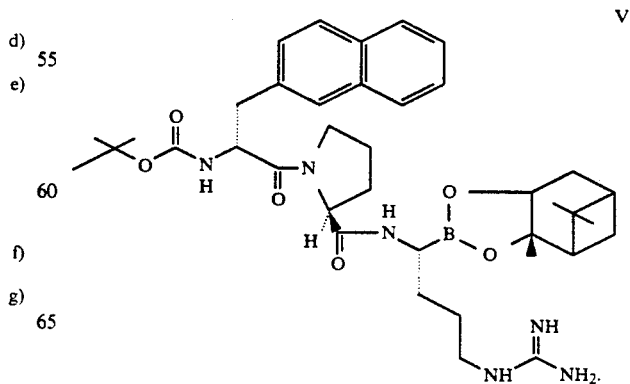

11. Therapeutical composition useful in inhibition of trypsin-like serine proteases containing a compound of claims 1 or 2 together with pharmaceutically acceptable additives and/or diluents.

12. Therapeutical composition according to claim 11 characterised in that trypsin-like serine proteases are thrombin, factor $X_a$, kallikrein, plasmin, prolyl endopeptidase and Ig AI protease.

13. Therapeutical composition having anti-thrombogenic activity containing a compound of claim 1 or 2 together with pharmaceutically acceptable additives and/or diluents.

* * * * *